US010568567B1

(12) United States Patent
Ford et al.

(10) Patent No.: US 10,568,567 B1
(45) Date of Patent: *Feb. 25, 2020

(54) METHOD OF DRUG APPROVAL USING MOTION VECTOR ANALYSIS

(71) Applicant: Vium, Inc, San Mateo, CA (US)

(72) Inventors: Daniel J. Ford, San Francisco, CA (US); Jonathan Betts-Lacroix, Belmont, CA (US)

(73) Assignee: Vium, Inc, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,859

(22) Filed: Jan. 21, 2019

Related U.S. Application Data

(63) Continuation-in-part of application No. 15/168,489, filed on May 31, 2016, now Pat. No. 10,188,321.

(51) Int. Cl.
*A61B 5/00* (2006.01)
*A61B 5/11* (2006.01)
*G06T 7/00* (2017.01)

(52) U.S. Cl.
CPC .......... *A61B 5/4839* (2013.01); *A61B 5/0077* (2013.01); *A61B 5/1113* (2013.01); *A61B 5/1121* (2013.01); *G06T 7/0016* (2013.01); *A61B 5/4528* (2013.01); *A61B 2503/40* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 6,611,206 B2* | 8/2003 | Eshelman | ............... | G06Q 50/22 128/920 |
| 8,065,180 B2* | 11/2011 | Hufford | ................ | G06F 19/325 705/7.38 |
| 9,700,257 B1* | 7/2017 | Betts-Lacroix | .......... | A61B 5/42 |
| 2009/0187392 A1* | 7/2009 | Riskey | ................. | A01K 11/007 703/11 |
| 2009/0298703 A1* | 12/2009 | Gough | .................. | G06T 7/0012 506/8 |
| 2010/0302004 A1* | 12/2010 | Winstead | ............. | A01K 29/005 340/7.32 |

(Continued)

OTHER PUBLICATIONS

Serre, Thomas, et al. "Automated home-cage behavioral phenotyping of mice." Nature (2009). (Year: 2009).*

(Continued)

*Primary Examiner* — Samah A Beg
(74) *Attorney, Agent, or Firm* — Kim Rubin

(57) ABSTRACT

A method of treating a patient for a disease, such as arthritis, is described. Steps include treating an animal for the disease with a first treatment, capturing video frames, then using optical flow to compute vector fields for each frame, then taking a maximum vector value over a first time period, then selecting a set of maximum vector values over a second time period, then clipping those values to a maximum, and then computing an average of those values. This value is an efficacy and it is compared to a baseline efficacy. If the treatment is efficacious, the patient is so treated. A method of applying for a drug for approval is also described, using substantially the same steps.

2 Claims, 12 Drawing Sheets

(56) References Cited

U.S. PATENT DOCUMENTS

| | | | | |
|---|---|---|---|---|
| 2012/0150048 A1* | 6/2012 | Kang | ............... | A61B 6/508 600/481 |
| 2013/0029909 A1* | 1/2013 | Ryan | ............... | C07D 491/22 514/8.1 |
| 2013/0079599 A1* | 3/2013 | Holmes | ............... | G06F 19/3418 600/300 |
| 2013/0267794 A1* | 10/2013 | Fernstrom | ............... | G01N 33/02 600/301 |
| 2013/0302412 A1* | 11/2013 | Ramaekers | ............... | A61K 38/446 424/451 |
| 2015/0039239 A1* | 2/2015 | Shuler | ............... | A61B 5/0022 702/19 |
| 2015/0223733 A1* | 8/2015 | Al-Alusi | ............... | G01S 13/87 600/479 |
| 2015/0237834 A1* | 8/2015 | Schab | ............... | A01K 29/005 340/573.3 |
| 2016/0320405 A1* | 11/2016 | Barbosa | ............... | G16H 20/10 |
| 2018/0092591 A1* | 4/2018 | Ford | ............... | A61B 5/4076 |
| 2018/0092596 A1* | 4/2018 | Ford | ............... | A61B 5/4076 |
| 2018/0092605 A1* | 4/2018 | Schaevitz | ............... | A61B 5/7275 |
| 2019/0191665 A1* | 6/2019 | Schaevitz | ............... | A01K 1/031 |
| 2019/0274625 A1* | 9/2019 | Ford | ............... | A61B 5/4848 |

OTHER PUBLICATIONS

Steele, Andrew D., et al. "The power of automated high-resolution behavior analysis revealed by its application to mouse models of Huntington's and prion diseases." Proceedings of the National Academy of Sciences 104.6 (2007): 1983-1988. (Year: 2007).*

* cited by examiner

Fig. 1

```python
# arthritis_index.py
"""

Computes the arthritis index (peak motion) given a cage and a day zero

"""

from analytics.core import stats
from sdk import from_s3
from sdk import from_kairos
from sdk import mus
from common import log
from common.utils import utime
from common.utils.utime import ONEDAY, ONEHOUR
from common.metrics import metric_client
from common.metrics import metric_data
from common.metrics import metric_source_naming import math
import numpy as np
import gflags gflags.DEFINE_bool('arthritis_index_testing', False, 'Is the arthritis index in testing mode?')
gflags.DEFINE_bool('arthritis_use_kairos', False, 'Use Kairos to load motion data for Arthritis Index?')
DAI_SHIFT = 1.8 def compute_magic_number(x, LIMIT=30, clip_speed=0.8):
    shift = 0
    vv = None
    highest_points = []
    x = x[(-x[:,1]).argsort()]
    n = math.ceil(len(x)*0.05)
    if n < LIMIT:   # Just for now.... # NOTE: REMOVE THIS LATER!!!
        log.info("XXXXX SKIPPING: %s < %s" % (n, LIMIT))
    else:
        n = 36 # It's just a magic number  # Probably should use N... or err on the side of caution...
        highest_vals = x[shift:(n+shift), 1]
        #hv_base = copy.copy(highest_vals)
        highest_vals = np.clip(highest_vals, a_min=0, a_max=clip_speed)
        highest_points = x[shift:(n+shift),]
        vv = highest_vals.mean()
    return vv, highest_points
```

Fig. 2

```
def find_fastest_times_in_night(cage, t, shift=7*ONEHOUR, return_points=False, exp_day_zero=None):
    midnight = utime.start_of_day(t)
    interval = utime.Interval(midnight - 7*ONEHOUR, midnight + 8*ONEHOUR - 0.0001)

get_fn = from_s3.get
    if gflags.FLAGS.arthritis_use_kairos:
        get_fn = from_kairos.get
    t = utime.now()
    data1 = get_fn(cage, 'motion.60s.max', '4', interval)
    data1.data = from_s3.clean_dupe_timestamps(data1.data)
    #exit(1)
    if False:
        data2 = data1
    else:
        data2 = get_fn(cage, 'motion.60s.max', '4.0', interval)
        data2.data = from_s3.clean_dupe_timestamps(data2.data)
    log.info("Loading time %s for %s %s" % (utime.now()-t, cage, interval.to_string()))
    if (len(data1.data) > 910 or len(data2.data) > 910):
        log.error("Bad number of data points loaded: %s %s for %s %s" %
                (len(data1.data), len(data2.data), cage, interval.to_string()))
        raise Exception("Bad data loading: got %s and %s points where at most %s each are allowed" % (len(data1.data), len(data2.data), 910))
    data = np.vstack([data1.data, data2.data])
    data = from_s3.clean_dupe_timestamps(data)

log.info("LEN data = %s (%s %s) for %s %s" % (len(data), len(data1.data), len(data2.data), cage, interval.to_string(tz='+07:00')))

vv = None
    highest_points = []
    if len(data) > 0:
        vv, highest_points = compute_magic_number(data)

if exp_day_zero is not None:
        log.info("%s %s" % ((midnight - exp_day_zero)/utime.ONEDAY, vv))

if not return_points:
        return vv
    return vv, highest_points
```

Fig. 3

```
def peak_motion(cage, interval, exp_day_zero=None):
   log.check_ne(interval.end_time_sec, np.Inf)
   #log.info("peak_motion time_range = %s " % (interval.to_string()))
   ts = []
   t = interval.start_time_sec
   t = utime.middle_of_day(t)
   t += 2*ONEDAY  # Completely ignore the first two days of data: acclimation.
   while t < interval.end_time_sec + 2 * ONEDAY:
      # NOTE: Should probably only be 1 day...
      vv, _ = find_fastest_times_in_night(cage, t, return_points=True, exp_day_zero=exp_day_zero)
      if vv is not None:
         ts += [[utime.middle_of_day(t), vv]]
      t += ONEDAY
   return ts def normalize_scores_2(ref_vals, ts, exp_day_zero):
   ss = stats.compute_summary_stats(ref_vals)
   if ss['sd'] == 0:
      print "UP"
      ss['sd'] = 1  # Won't matter since all points will be set to zero anyway
   ss['sd'] = max(ss['sd'], 0.0001)
   sd = max(ss['sd'], 0.04)
   sd = min(sd, 0.05)
   def norm_scores(timeseries, mean, sd):
      return map(lambda x: [x[0], (x[1]-mean)/sd], timeseries)
   scores = norm_scores(ts, ss['mean'], -1*sd)

if True:
      norm_ref_vals = map(lambda x: x[1], filter(lambda x: baseline_filter(x, exp_day_zero), scores))
      #log.info("NRV mean = %s" % (np.array(norm_ref_vals).mean()))
      assert( abs(np.array(norm_ref_vals).mean()) < 0.0001)
   return scores def baseline_filter(point, exp_day_zero=0):
   t = point[0] - exp_day_zero
   if t < - 2*ONEDAY:
      return False
   if t > 6*ONEDAY:
      return False
   if t < 1*ONEDAY and t > 0:
      return False
   return True
```

Fig. 4

```
def compute_arthritis_index_inner(cage, exp_day_zero, interval):
    ts = peak_motion(cage, interval, exp_day_zero)
    ref_vals = map(lambda x: x[1], filter(lambda x: baseline_filter(x, exp_day_zero), ts))
    log.info("Reference_values = %s" % (map(lambda x: "%.3f" % (x,), ref_vals)))
    if len(ref_vals) == 0:
        return np.zeros((0,2))
    #ss = stats.compute_summary_stats(ref_vals)
    scores = normalize_scores_2(ref_vals, ts, exp_day_zero)
    if len(scores) > 0:
        scores = np.array(scores)
    else:
        scores = np.zeros((0,2))
    scores[:,1] = scores[:,1] + DAI_SHIFT
    return scores def compute_arthritis_index(cage):
    interval = cage.slotted_interval()
    if interval is None:
        log.info("Interval for cage %s is None. Returning." % (cage))
        return np.zeros((0,2))
    if interval.end_time_sec == np.Inf:
        interval.end_time_sec = utime.now()
    #log.info('%s %s' % (interval.start_time_sec, interval.end_time_sec))
    exp_day_zero = cage.day_zero()

log.info("%s %s %s %s" % (cage, exp_day_zero, interval, utime.to_string(exp_day_zero)))
    scores = compute_arthritis_index_inner(cage, exp_day_zero, interval)
    import copy
    s2 = copy.copy(scores)
    s2[:,0] -= exp_day_zero
    s2[:,0] /= utime.ONEDAY
    log.info("%s len=%s \nscores= %s" % (cage, len(s2), str(s2)))
    return scores
```

Fig. 5

```
def compute_arthritis_index(cage):
    interval = cage.slotted_interval()
    if interval is None:
        log.info("Interval for cage %s is None. Returning." % (cage))
        return np.zeros((0,2))
    if interval.end_time_sec == np.Inf:
        interval.end_time_sec = utime.now()
    #log.info('%s %s' % (interval.start_time_sec, interval.end_time_sec))
    exp_day_zero = cage.day_zero()

log.info("%s %s %s %s" % (cage, exp_day_zero, interval, utime.to_string(exp_day_zero)))
    scores = compute_arthritis_index_inner(cage, exp_day_zero, interval)
    import copy
    s2 = copy.copy(scores)
    s2[:,0] -= exp_day_zero
    s2[:,0] /= utime.ONEDAY
    log.info("%s len=%s \nscores= %s" % (cage, len(s2), str(s2)))
    return scores def compute_and_save_arthritis_index(mus_object, write=True):
    scores = compute_arthritis_index(mus_object)
    output_metric_name = 'arthritis_index'
    if gflags.FLAGS.arthritis_index_testing:
        output_metric_name = 'testing.' + output_metric_name
    write_version = 2.0
    if isinstance(mus_object, mus.Cage):
        source = metric_source_naming.get_cage_source(mus_object.id())
    elif isinstance(mus_object, mus.Subject):
        source = metric_source_naming.get_subject_source(mus_object.id())
    else:
        raise RuntimeError("mus_object %s of type %s must be a Subject or a Cage." %
                (mus_object, type(mus_object)))
    log.info("Source = %s" % (source))
    if write:
        # TODO: check the source here
        log.info("Source = %s" % (source))
        mclient = metric_client.MetricClient()
        mclient.put_metrics(source, [{
            metric_data.METRIC_NAME_KEY:output_metric_name,
            metric_data.METRIC_TAGS_KEY:{'version':write_version, 'type':'synthetic'},
            metric_data.METRIC_VALUES_KEY:scores
        }])
        log.info("Successfully wrote %s points for %s" % (len(scores), source))
    if len(scores) > 0:
        scores = np.array(scores)
    else:
        scores = np.zeros((0,2))
    return scores
```

METHOD OF DRUG APPROVAL USING MOTION VECTOR ANALYSIS

This application is a continuation-in-part of parent application Ser. No. 15/168,489 filed on 31 May 2016.

BACKGROUND OF THE INVENTION

Prior art methods of determining the degree of arthritis of a rodent are use of calipers to measure the swelling of a joint, or have the joint sectioned and laboratory analyzed by histopathology. The first method disturbs the animal and produces inconsistent results. The second method is expensive, slow, and works only on dead animals.

SUMMARY OF THE INVENTION

Embodiments of this invention use a video camera to observe animal behavior in the animals' comfortable environment, such as rodents in their home cage. Motion of the animal is detected and analyzed by methods described. A metric for animal health, such as degree of arthritis, is then computed. Embodiments include comparing a plot of the animal health metric over time with other plots to determine health, disease, efficacy of a drug or therapy, behavior characteristics, breed line characteristics, and the like.

Descriptions and scenarios are non-limiting examples.

Embodiments record video of a cage interior continuously, at 24 frames per second. These frames are transmitted to a computation facility where they are analyzed after real-time. Some embodiment use real time analysis. Some embodiments perform part or all of the method steps at the cage or in the camera.

Exemplary steps are:

1) Record video of a cage interior that comprises one or more animals.
2) Transmit digital video to a computation facility for storage and computation.
3) Dewarp the images responsive to the layout of the cage, camera position and angle. Optionally correct for distance, parallax and camera lens distortion. Optionally correct for non-uniform lighting or vignetting.
4) Optionally perform masking to remove uninteresting areas of the frame.
5) Use optical flow analysis to produce a reduced vector field for each frame.
6) Select one or more maximum vectors from the field.
7) Record the highest vector amplitude value of all vectors in all fields over one minute of frames.
8) Select the highest 36 values during a 14-hour nocturnal period; or the highest 5% in the period.
9) Optionally clip the values from the previous step to a predetermined threshold.
10) Take the mean of the values from the previous step.
11) The value from the previous step is a nightly motion scalar
12) Determine a baseline of nightly motion scalars for an animal or subject group. Average this baseline, or selectively perform the above processing steps to create a baseline.
13) Measure nightly motion scalars for the animal(s) under study for the time period of the study.
14) Subtract the baseline value from the nightly motion scalar(s) of the previous step. The result of each subtraction is an animal health metric for that day (or night).
15) Optionally normalize the value from the previous step.
16) The result from the previous step comprises a plot of the animal health metrics with one point per night per animal.

BRIEF DESCRIPTION OF THE DRAWINGS

FIG. 1 shows a first page of a code listing to implement an embodiment of the method.
FIG. 2 shows a second page of the code listing to implement an embodiment of the method.
FIG. 3 shows a third page of the code listing to implement an embodiment of the method.
FIG. 4 shows a fourth page of the code listing to implement an embodiment of the method.
FIG. 5 shows a fifth page of the code listing to implement an embodiment of the method.

DETAILED DESCRIPTION

Figure 11:
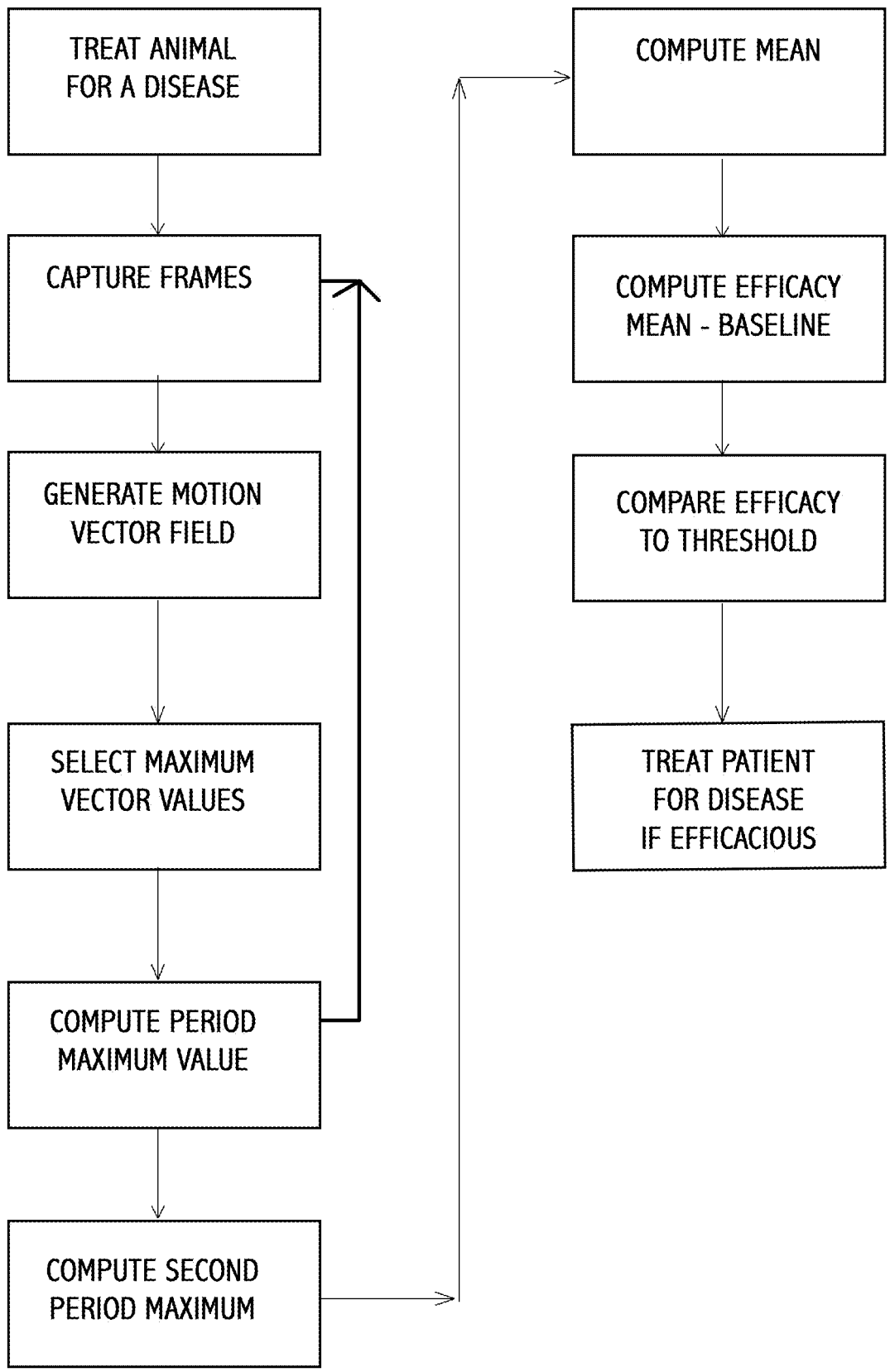
FIG. 11 shows a block diagram of an embodiment for a method of treating a patient after a treatment has been determined to be efficacious.

FIG. 11 shows an embodiment of a method of this invention where a test animal is treated for a particular disease with a particular drug. In other embodiments different treatments using the same drug or similar treatments using a different drug, or combinations of a drug. At the conclusion of the method a patient may be treated for the disease using the same treatment, with such modifications as necessary and known in the art to convert an animal treatment to a human or other animal treatment.

In step 1, an animal, typically in a cohort in a vivarium, is treated for a first disease with a first treatment.

In step 2, frames are captured with one or two video cameras or other image capture device(s). Video may be from a monochrome camera, a visual light color camera, an infrared camera, a thermal camera, or any hybrid or combination. A "frame" may be a single camera frame or may be a subset, combination, or aggregation of frames from one or more cameras. IR light may be used to illuminate a cage for an IR sensitive camera, particularly during a nocturnal period for an animal. A frame rate may be 24 frames per second, or another rate.

Following step 2, optional dewarping occurs. Dewarping to create an equivalent frame to an overhead view of a cage means creating a frame sufficiently uniform, such as pixels/inch and illumination, to meet the needs of the method. Significant non-uniformity following the dewarping may be acceptable. For example, remaining distortion or warp in the range of 10% to 50% may be acceptable. Dewarping is for the purpose of having a given motion vector value in the motion vector field correspond to given amount of animal motion independent of the position of the animal in the cage. In some embodiments, the dewarping step may be a null step. For example, if a camera is looking straight down into the cage from the center of the cage, even with lens distortion and parallax errors, an explicit dewarping step may not be required. As another example, the view may be for only a portion of a cage, and distortion over that portion does not require dewarping. We specifically claim embodiments with no dewarping, and also embodiments with various dewarping algorithms as known in the art.

Frames may be distorted with respect to vertical and horizontal proportions, parallax, or aspect ratio.

Step 3 generates a motion vector field using optical flow. The motion vector field shape need not be square. Typically, the vector field is roughly the same shape as the aspect ratio of the frames. The vector field may have a different aspect ratio so that each vector in the field represents motion in a square area. Exemplary motion vector field sizes range from 4 to 10,000 vectors per frame, or from 16 to 1600 vectors per frame. An exemplary vector field may be 15×20 vectors. Frames may be decimated or some frames may be skipped or some frames may be selected prior to this step. For example, frames with motion (vector amplitudes) below a threshold may be skipped; frames with motion only in certain portions of a frame may be skipped.

Optical flow methods are known in the art, such as Lucas-Kanade, Horn-Schunck, Buxton-Buxton, and Black-Jepson. A suitable method is Farnebäck.

Step four selects one or more frame maximum motion values from the vector field. Maximum vector amplitude means taking the amplitude of a vector. That is, ignoring its direction. Some embodiments may consider direction. Vector direction may be used as selection criteria for the vector or as a weighting factor.

One embodiment selects one maximum amplitude vector from each vector field. Other embodiments select set of maximum vector values, such as a set of three. Selected vectors may be averaged; they may also be subject to validation.

Motion vector value may be clipped to a predetermined maximum or percentage threshold. The purpose of this is to remove artifacts, such as a mouse poking the camera lens, or motion from a lab attendant moving or servicing a cage, and the like. Large artifact motions interfere with creating a meaningful average of real rodent motion, and thus are ideally removed. Such clipping may be considered part of the selecting frame motion value step, or may be claimed as a separate step.

Image masking may occur at any step of the method, from optical masking in front of the camera lens, to masking within the camera, to masking of raw images, to masking of images after dewarping, to masking the vectors in the vector field. Masking does two things. First, it eliminates parts of the image that are not interesting, such as areas inaccessible to the animal. Second, it eliminates parts of the image that may produce artifacts, such as reflection from water in a water bottle, views out through a portion of a clear cage, motion from servicing the cage or animal, and the like. Masks may be fixed or may be determined dynamically or empirically.

Step five selects a first period motion value. A first period may be one minute or another period value. One embodiment selects the largest n motion values for the period, then takes the mean. Another embodiment uses the largest motion value over the period, such as one minute. A first period may be as short as one frame or as long as a day.

Step 5 is repeated, including however many necessary prior steps, such as steps 2, 3, 4 and 5. At the end of step five there are one or more motion values for each first period.

Step 6 creates a maximum value set from all of the motion values for all first periods within a second period. A second period may be a 14-hour night, or another period. A second period may be as short as a second, a minute, or an hour. One embodiment creates the maximum value set by selecting the highest 36 values from the entire first period motion values. Another embodiments selects the top 4% or 5% of all first period motion values. For example, if the first period is one minute, and the second period is 14 hours, there are 60*14 minutes in 14 hours, so there will be approximately 900 first period motion values.

Following step 6 is an optional clipping step, where each value in the maximum value set is compared to a threshold. If the value is over the threshold it is reduced to the threshold value. This step removes large motion artifacts, such as might be caused by a nose poke at the camera lens or an action by a technician.

Step 7 computes the mean of the optionally clipped values in the maximum value set. Other averaging methods, including data weighting, as known in the art, may be used. At this point, there is a single motion scalar for the animal for the second time period, such as one day (or night).

Step 8 computes efficacy of threating the animal with the drug by subtracting a baseline value from the computed mean. This baseline motion value may be known in advance, or computed before, during or after steps of embodiments. The baseline value may be computed using the same or similar prior steps of the method. See FIGS. 7 and 8 for exemplary baseline periods. After step 8 there is again a single motion scalar for the animal for the second time period. This value may be considered "activity" motion over the animal's baseline motion, Step 9 compares the efficacy computed in the prior step a threshold value. Such a threshold may be efficacy of a different drug or different treatment, or efficacy of no treatment.

Step 10 treats a patient for the disease if the treatment is efficacious, as determined in the previous step.

Figure 12:
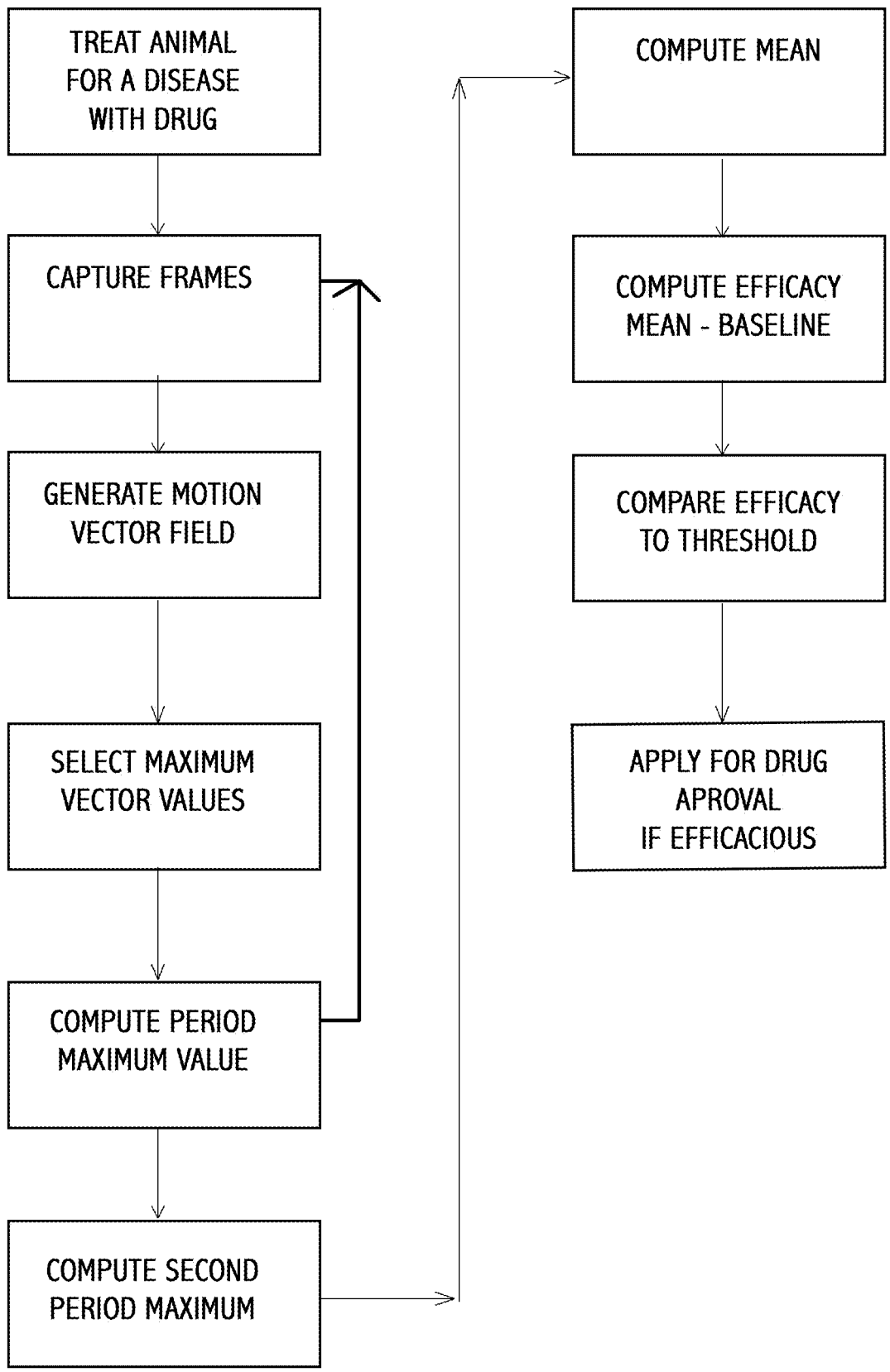
FIG. 12 shows block diagram of an embodiment for a method of applying for approval of a drug after a treatment using the drug has been determined to be efficacious.

FIG. 12 shows an embodiment of a method of this invention where a test animal is treated for a particular disease with a particular drug. If the treatment is successful, application, such as the US FDA, may be made for approval of the drug for treatment of the disease.

In step 1, an animal, typically in a cohort in a vivarium, is treated for a first disease with a first drug.

In step 2, frames are captured with one or two video cameras or other image capture device(s). Video may be from a monochrome camera, a visual light color camera, an infrared camera, a thermal camera, or any hybrid or combination. A "frame" may be a single camera frame or may be a subset, combination, or aggregation of frames from one or more cameras. IR light may be used to illuminate a cage for an IR sensitive camera, particularly during a nocturnal period for an animal. A frame rate may be 24 frames per second, or another rate.

Following step 2, optional dewarping occurs. Dewarping to create an equivalent frame to an overhead view of a cage means creating a frame sufficiently uniform, such as pixels/inch and illumination, to meet the needs of the method. Significant non-uniformity following the dewarping may be acceptable. For example, remaining distortion or warp in the range of 10% to 50% may be acceptable. Dewarping is for the purpose of having a given motion vector value in the motion vector field correspond to given amount of animal motion independent of the position of the animal in the cage. In some embodiments, the dewarping step may be a null step. For example, if a camera is looking straight down into the cage from the center of the cage, even with lens distortion and parallax errors, an explicit dewarping step may not be required. As another example, the view may be for only a portion of a cage, and distortion over that portion does not require dewarping. We specifically claim embodiments with no dewarping, and also embodiments with various dewarping algorithms as known in the art.

Frames may be distorted with respect to vertical and horizontal proportions, parallax, or aspect ratio.

Step 3 generates a motion vector field using optical flow. The motion vector field shape need not be square. Typically, the vector field is roughly the same shape as the aspect ratio of the frames. The vector field may have a different aspect ratio so that each vector in the field represents motion in a square area. Exemplary motion vector field sizes range from 4 to 10,000 vectors per frame, or from 16 to 1600 vectors per frame. An exemplary vector field may be 15×20 vectors. Frames may be decimated or some frames may be skipped or some frames may be selected prior to this step. For example, frames with motion (vector amplitudes) below a threshold may be skipped; frames with motion only in certain portions of a frame may be skipped.

Optical flow methods are known in the art, such as Lucas-Kanade, Horn-Schunck, Buxton-Buxton, and Black-Jepson. A suitable method is Farnebäck.

Step four selects one or more frame maximum motion values from the vector field. Maximum vector amplitude means taking the amplitude of a vector. That is, ignoring its direction. Some embodiments may consider direction. Vector direction may be used as selection criteria for the vector or as a weighting factor.

One embodiment selects one maximum amplitude vector from each vector field. Other embodiments select set of maximum vector values, such as a set of three. Selected vectors may be averaged; they may also be subject to validation.

Motion vector value may be clipped to a predetermined maximum or percentage threshold. The purpose of this is to remove artifacts, such as a mouse poking the camera lens, or motion from a lab attendant moving or servicing a cage, and the like. Large artifact motions interfere with creating a meaningful average of real rodent motion, and thus are ideally removed. Such clipping may be considered part of the selecting frame motion value step, or may be claimed as a separate step.

Image masking may occur at any step of the method, from optical masking in front of the camera lens, to masking within the camera, to masking of raw images, to masking of images after dewarping, to masking the vectors in the vector field. Masking does two things. First, it eliminates parts of the image that are not interesting, such as areas inaccessible to the animal. Second, it eliminates parts of the image that may produce artifacts, such as reflection from water in a water bottle, views out through a portion of a clear cage, motion from servicing the cage or animal, and the like. Masks may be fixed or may be determined dynamically or empirically.

Step five selects a first period motion value. A first period may be one minute or another period value. One embodiment selects the largest n motion values for the period, then takes the mean. Another embodiment uses the largest motion value over the period, such as one minute. A first period may be as short as one frame or as long as a day.

Step 5 is repeated, including however many necessary prior steps, such as steps 2, 3, 4 and 5. At the end of step five there are one or more motion values for each first period.

Step 6 creates a maximum value set from all of the motion values for all first periods within a second period. A second period may be a 14-hour night, or another period. A second period may be as short as a second, a minute, or an hour. One embodiment creates the maximum value set by selecting the highest 36 values from the entire first period motion values. Another embodiments selects the top 4% or 5% of all first period motion values. For example, if the first period is one minute, and the second period is 14 hours, there are 60*14 minutes in 14 hours, so there will be approximately 900 first period motion values.

Following step 6 is an optional clipping step, where each value in the maximum value set is compared to a threshold. If the value is over the threshold it is reduced to the threshold value. This step removes large motion artifacts, such as might be caused by a nose poke at the camera lens or an action by a technician.

Step 7 computes the mean of the optionally clipped values in the maximum value set. Other averaging methods, including data weighting, as known in the art, may be used. At this point, there is a single motion scalar for the animal for the second time period, such as one day (or night).

Step 8 computes efficacy of threating the animal with the drug by subtracting a baseline value from the computed mean. This baseline motion value may be known in advance, or computed before, during or after steps of embodiments. The baseline value may be computed using the same or similar prior steps of the method. See FIGS. 7 and 8 for exemplary baseline periods. After step 8 there is again a single motion scalar for the animal for the second time period. This value may be considered "activity" motion over the animal's baseline motion, Step 9 compares the efficacy computed in the prior step a threshold value. Such a threshold may be efficacy of a different drug or different treatment, or efficacy of no treatment.

Step 10 applies for approval of the drug if the treatment is efficacious as determined in the previous step.

When the shape of an animal health profile is compared to animal health profiles of other animals that have died to compute an expected time to die of the animal of the animal health profile, such comparison may be a "best fit" algorithm, as is known in the art. Computed expected time to die may be a computed mean or a statistical metric, such as a mean and standard deviation.

The baseline motion for an animal may be taken over a period of 2 to 20 days. Typically, an animal should rest for 1 to 5 days after being moved before the baseline is taken. Baseline may be before, after, or both, of "day 0" where "day 0" is the day of a treatment or start of a treatment or procedure. For most rodents, whose natural activity level is nocturnal, animal motions should be analyzed during this nocturnal period.

Note that in general most steps must inherently be performed in the order stated. However, some steps, such as image masking and baseline motion collection and computation, may be done at numerous points in the method, as those trained in the art know. Baseline motion collection or computation may be done before, during or after a study. It may be for the same animal or for different animals. Baseline data should be applicable to the animal(s) in the study. Baseline values may be clinically known.

Embodiments may be used to detect and quantify hyperactivity, pain, lethargy, seizures and any motor dysfunction. Embodiments may be used to detect and quantify behavior between animals, including grooming, fighting, mating, and nurturing, for example. Embodiments may be combined with any methods of identifying a specific animal in a cage, including video methods or electronic methods. Embodiments may be combined to identify motion from a specific animal or motion between two or more animal.

FIGS. 1-5 show an exemplary code listing of an implementation, in python.

Figure 6:
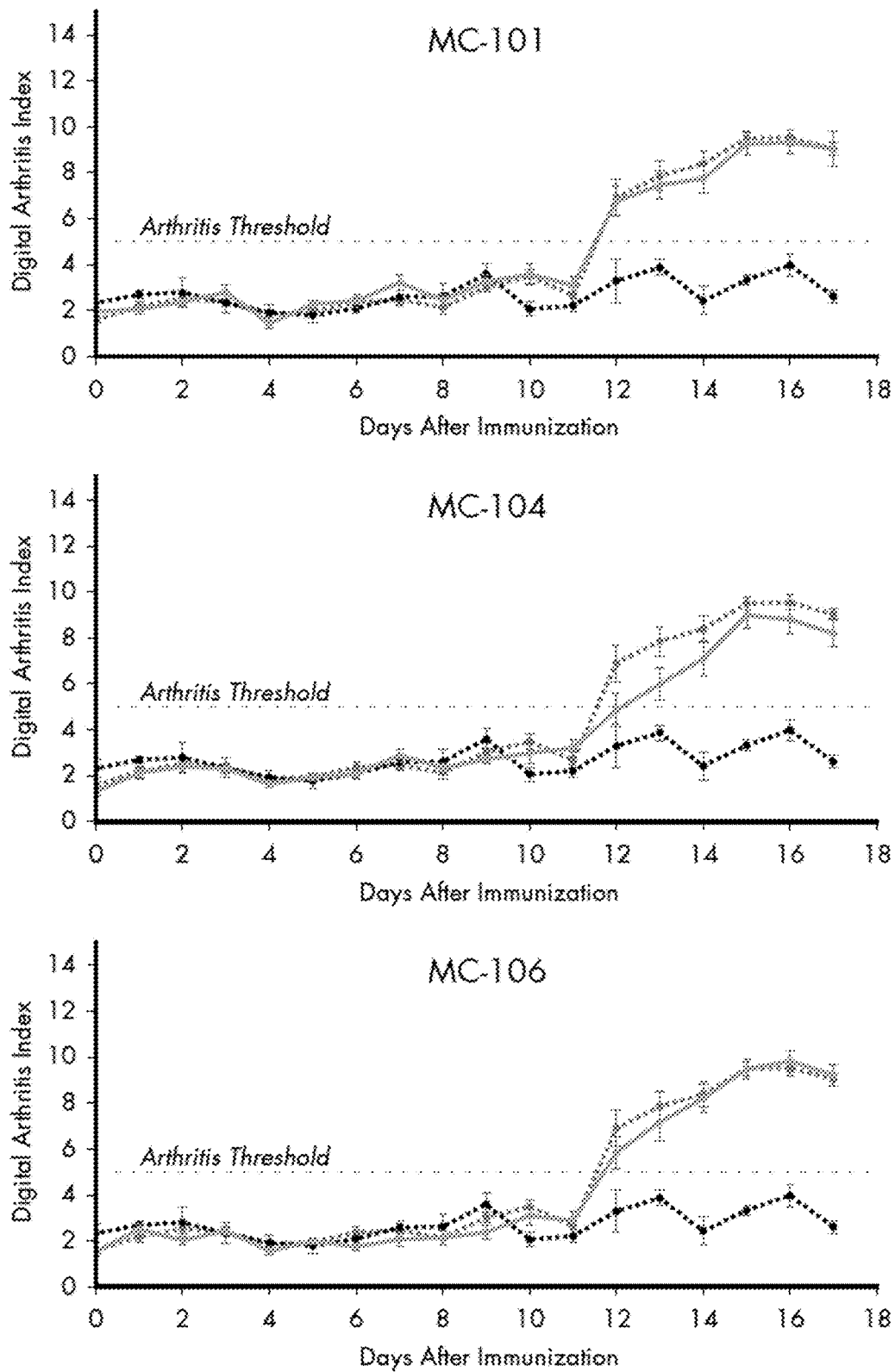
FIG. 6 shows three plots of an animal arthritis health index over time.

FIG. 6 shows measured animal health index for three animal subjects, MC-101, MC-104 and MC-106. Measured health indexes by an embodiment of the claimed methods are shown as the upper dotted lines, along with a one-sigma variation band. Arthritis measured by conventional prior art is also plotted, as the center, solid line, for each subject. A baseline motion is also shown for each subject, as the bottom dotted line, along with a one-sigma variation band. These charts are from a pre-publication validation paper by one of the inventors. Note that the values of the Arthritis index, also called a health index, have been normalized. Note also the horizontal dotted line, which is a clinically determined and accepted threshold for a binary determination of whether a subject animal has arthritis, or not. Note that for two of the three subjects, methods of this invention detect arthritis one day sooner than prior art methods. This is a benefit of embodiments of this invention over prior art.

Figure 7:
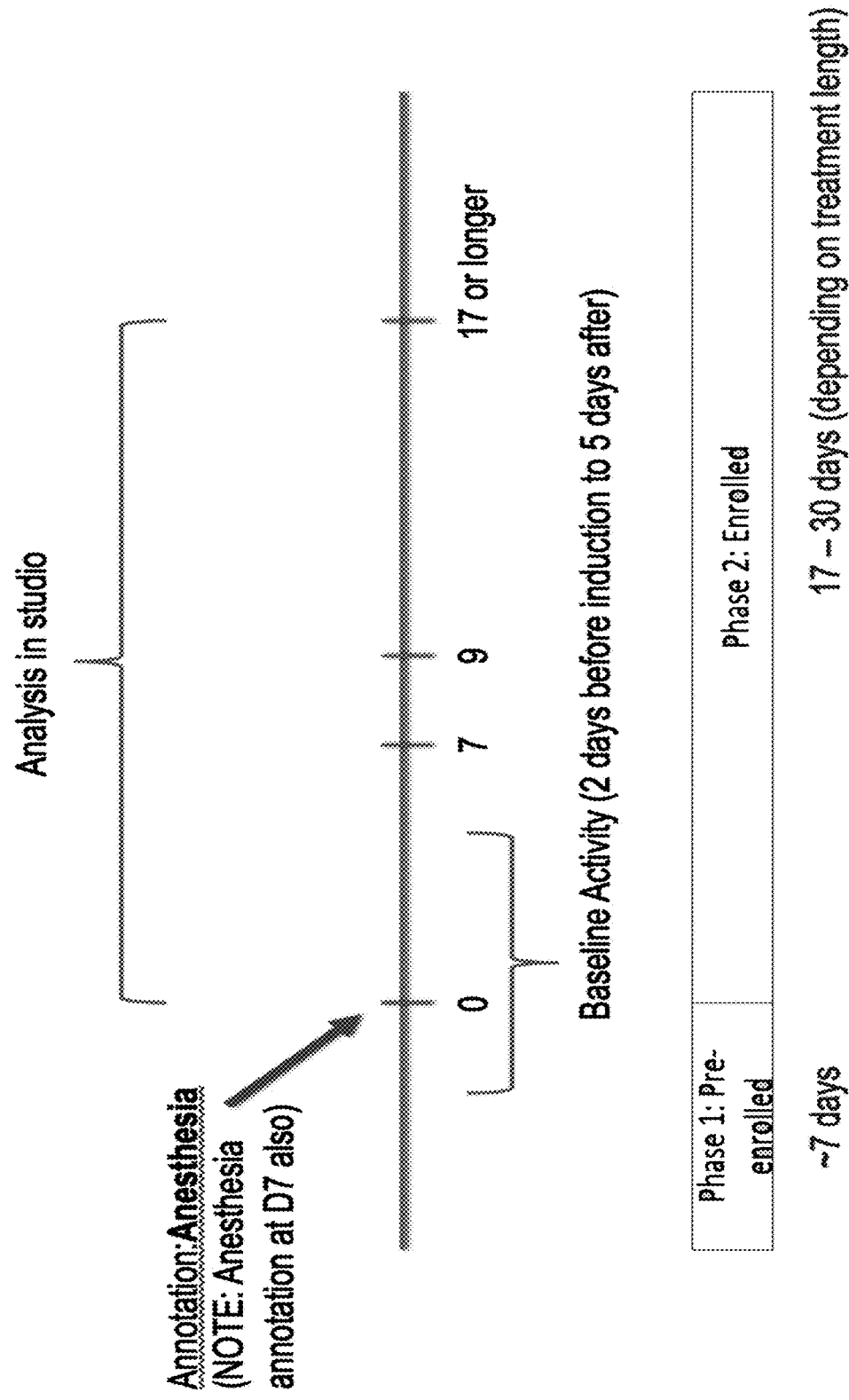
FIG. 7 shows a first exemplary baseline time period and study time period.

FIG. 7 shows a timeline for measuring baseline motion and the study period, or analysis period for subjects in a study. Here, baseline motion activity is measured both before and after an event, here, anesthesia. Some embodiments measure baseline motion activity only before an event. Some embodiments measure baseline motion activity only after an event. Note that baseline motion may not be measure the day of the event because the animal has been disturbed on this day and so the animal's motion is not indicative of baseline activity level.

Figure 8:
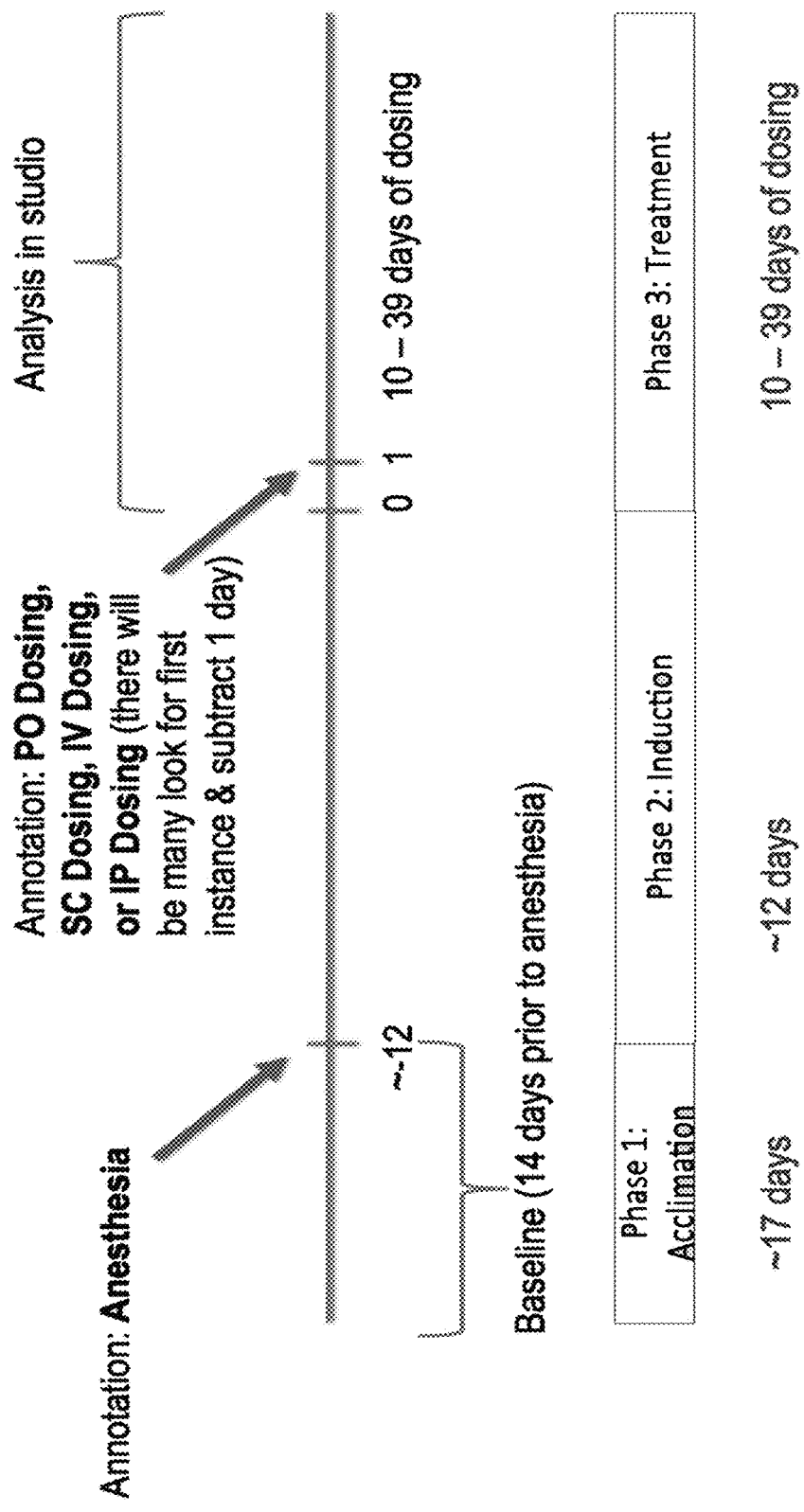
FIG. 8 shows a second exemplary baseline time period and study time period.
Figure 9:
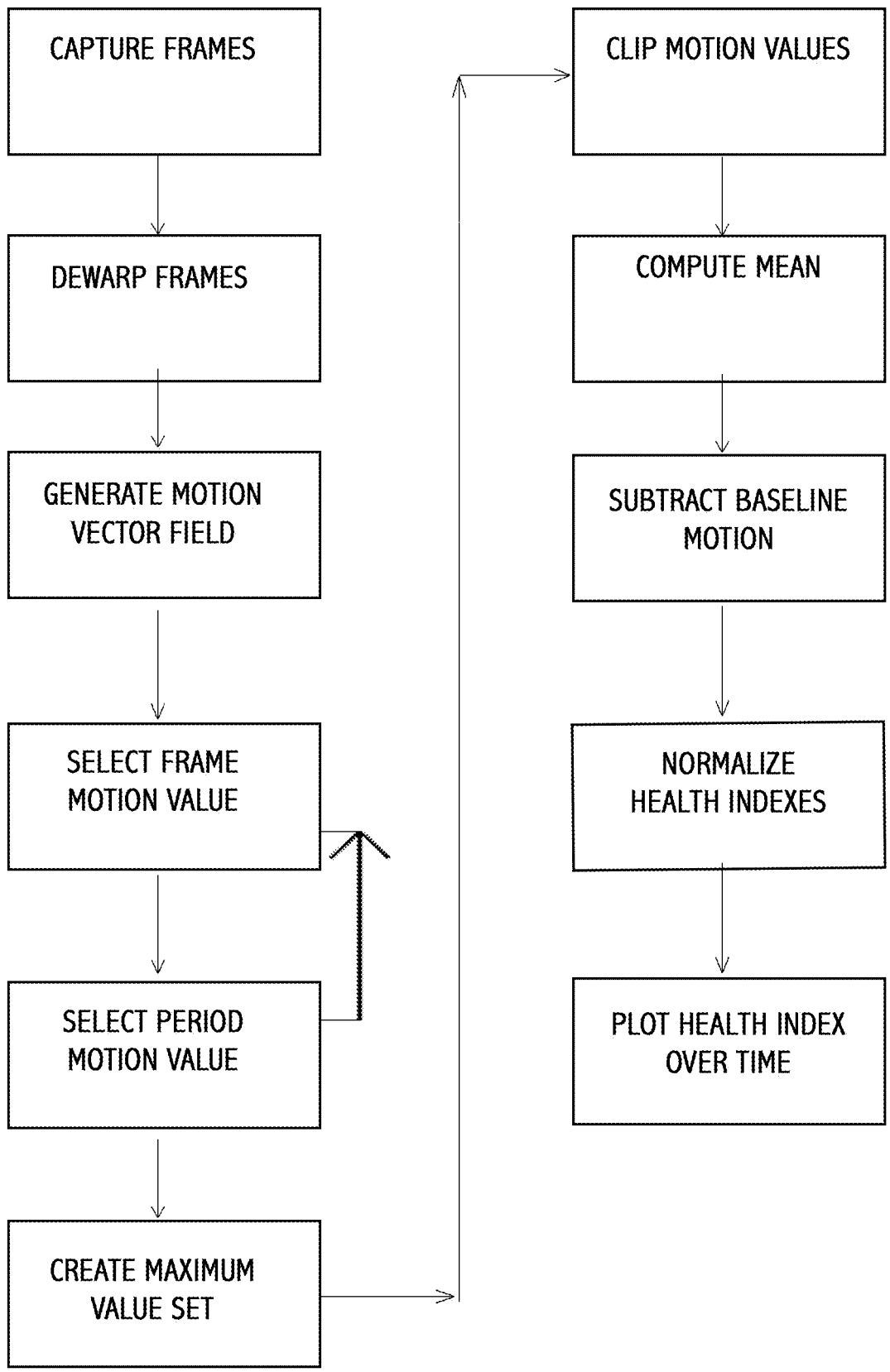
FIG. 9 shows a block diagram of one embodiment of the method.

FIG. 8 shows another timeline for measuring baseline motion. Here the baseline is only prior to anesthesia. Note for these study there are three phases, as shown.

Figure 10:
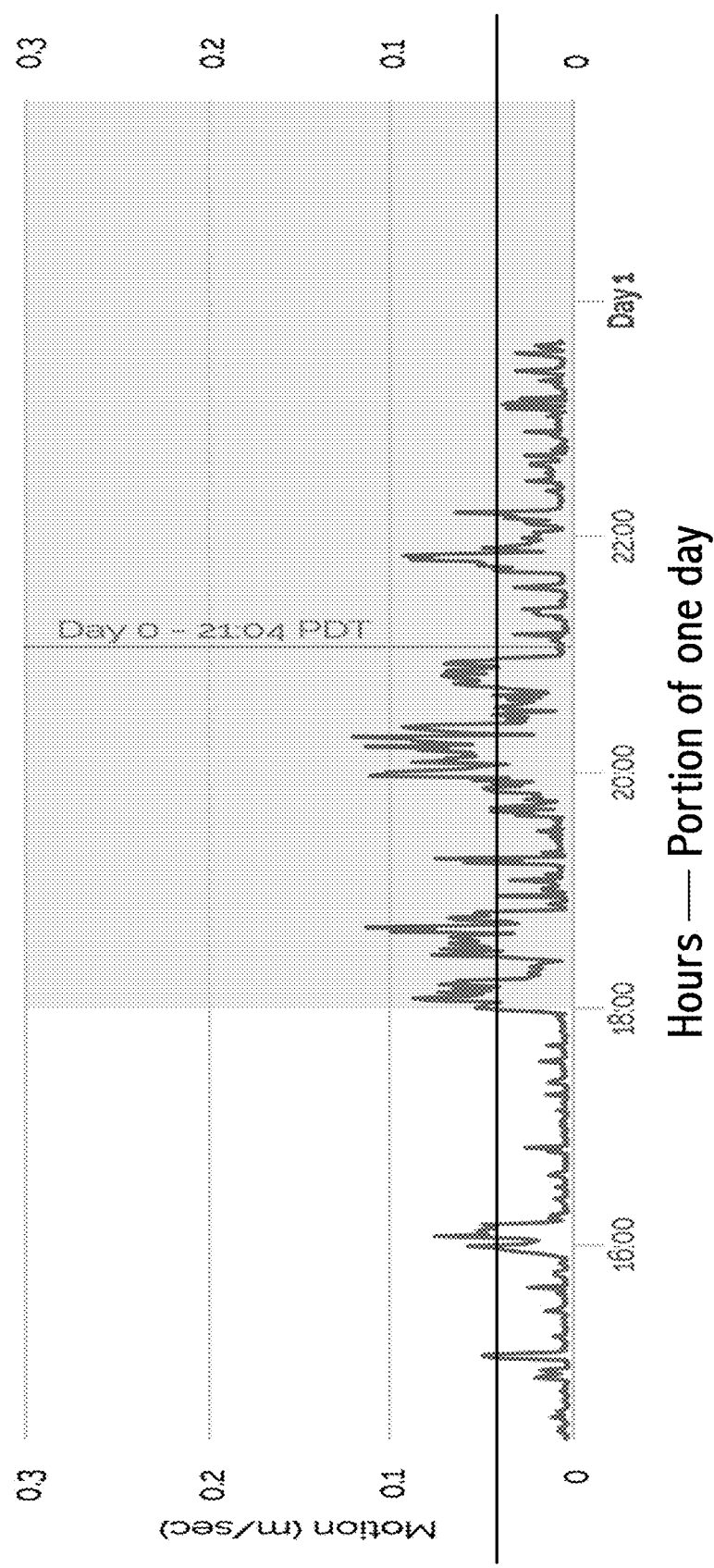
FIG. 10 shows a plot of one exemplary animal motion during a portion of a day and night period.

FIG. 10 shows a plot of one animal's measured motion during a portion of daytime and a portion of nighttime, for the animal. The nighttime period is shown as gray. Observe that the animals' natural activity period is nocturnal. Note that several activity levels are spikes above the clipping threshold. Here, the clipping threshold is 0.1 m/sec. These activities may be a mouse poking its nose at the camera lens, for example. Note the dark horizontal line, which represents an optional threshold for motion, as used in some embodiments. This threshold may be used to limit computational requirements by performing some computations, such as the motion vector field, to only those periods of motion above a threshold. Note that the motion during daylight may be used as a baseline. Note that the limited motion, such as around 16:00 may be included in computing a baseline or may be excluded, in which case the baseline is the activity below the dark threshold line, or below another threshold. Baseline motion may be computed on other days, as shown in previous Figures.

Definitions

"Dynamic" means may be performed without interrupting the operation of an operating vivarium in the cluster.

"IT" means "information technology."

"Sterile interior air"—Means pathogen-free interior air, in the context and meaning in the operation and art of operating vivariums.

"Pathogen-free"—means the population of microbes, including but not limited to bacteria, viruses, prions and toxins, relevant to an experiment, test or study ("study"), is sufficiently reduced to meet the needs of the study, or to impact or alter study results, or to alter the credibility or repeatability of study results, for studies using the vivarium, and to not impact the health, performance or behavior of the target animal population in the vivarium or of the workers.

"Subset"—May include any non-zero number of elements from a set, including all elements from the set.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims. Claims for devices and systems may be restricted to perform only the methods of embodiments or claims.

We claim:

1. A method for treating a patient for a first disease comprising the steps:
    (a) treating an animal for a first disease using a first treatment;
    (b) recording, using a camera, a series of image frames of an animal cage interior wherein the cage comprises the animal;
    (c) generating a reduced vector field from at least a subset of image frames from step (b) using optical flow analysis;
    (d) selecting one or more maximum vector values from the vector field from step (c);
    (e) computing a first-period maximum value for the one or more maximum vector values from step (d) over a first time period length;
    (f) repeating steps (b) through (e) for multiple, sequential time periods having the first time period length, wherein the multiple, sequential time periods fall within a second time period;

(g) selecting a second-period maximum value set from all of the first-period maximum values computed from repeating step (e);
(h) computing a mean value from the values of the second-period maximum value set selected from step (g);
(i) computing an efficacy of the first drug by subtracting a baseline value from the mean value from step (h);
(j) treating the patient with the first drug when the efficacy of the first drug computed in step (i) exceeds a predetermined threshold value.

2. A method for applying for approval of first drug for treating patients with a first disease, comprising the steps:
(a) treating an animal for a first disease using a first treatment;
(b) recording, using a camera, a series of image frames of an animal cage interior wherein the cage comprises the animal;
(c) generating a reduced vector field from at least a subset of image frames from step (b) using optical flow analysis;
(d) selecting one or more maximum vector values from the vector field from step (c);
(e) computing a first-period maximum value for the one or more maximum vector values from step (d) over a first time period length;
(f) repeating steps (b) through (e) for multiple, sequential time periods having the first time period length, wherein the multiple, sequential time periods fall within a second time period;
(g) selecting a second-period maximum value set from all of the first-period maximum values computed from repeating step (e);
(h) computing a mean value from the values of the second-period maximum value set selected from step (g);
(i) computing an efficacy of the first drug by subtracting a baseline value from the mean value from step (h); and
(j) applying for approval of the first drug when the efficacy of the first drug exceeds a predetermined threshold value.

* * * * *